US006238895B1

(12) United States Patent
Miers

(10) Patent No.: US 6,238,895 B1
(45) Date of Patent: *May 29, 2001

(54) PRODUCTION OF ASPARTIC AND MALIC ACIDS WITH MICROBACTERIUM

(75) Inventor: James M. Miers, Elkhart, IN (US)

(73) Assignee: Genencor International, Inc., Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/770,203

(22) Filed: Dec. 19, 1996

Related U.S. Application Data

(63) Continuation of application No. 08/365,402, filed on Dec. 28, 1994, now abandoned.

(51) Int. Cl.$^7$ ............................... C12P 13/04; C12P 7/46
(52) U.S. Cl. ..................... 435/109; 435/136; 435/145; 435/106; 435/107; 435/108
(58) Field of Search ..................... 435/106, 109, 435/107, 108, 136, 145

(56) References Cited

U.S. PATENT DOCUMENTS

| | | |
|---|---|---|
| 2,972,566 | 2/1961 | Kitahara . |
| 3,922,195 | 11/1975 | Chibata et al. . |
| 3,980,520 | 9/1976 | Degen et al. . |
| 4,138,292 | 2/1979 | Chibata et al. . |
| 4,486,532 | * 12/1984 | Chibata ................................ 435/145 |
| 4,912,043 | 3/1990 | Terasawa et al. . |

FOREIGN PATENT DOCUMENTS 2101903   7/1971   (DE) .

OTHER PUBLICATIONS

Chibata I, Hind. Antibiot. Bull, vol. 19–20, p. 58–67, 1978.*
Yukawa et al., Nippon Nogei Kagaku Kaishi, vol. 59, p. 31–37– 1985.*
Takata et al., Enzyme Microb. Technol., vol. 2(1), p. 30–36, 1990.*
Tosa et al., Ann. N.Y. Acad. Sci. vol. 542, p. 440–443, 1988
ATCC Catalogue of Bacteria, 1992, p. 190.*
Wan et al, Biotechnol. Appl. Biochem, vol. 10(2) p. 173–182, 1988.*
Goodfellow et al. "Biology of the Actinomycetes", 1984, Academic Press, p. 50–52 and 77–79.*
Tsuchida et al., Agric. Biol. Chem., 51(8), 2095–2101, 1987.*
Terasawa et al., Process Biochem., 20(4), 124–128, 1985.*
Yukawa et al, Process Biochem, 21(5), 164–166, 1986.*
T. Kawno et al., "Microbial Manufacture of L–malic Acid," Database Chemabs, Chemical Abstracts Service, Aug. 26, 1991, abstract No. 115:90693y.
T. Oyawa et al., "L–malic Acid by Fermintation," Chemical Abstracts, vol. 71, No. 3, Jul. 21, 1969, p. 234, column 1.
S. Watanabe et al., "Production of L–malic Acid by Bacteria," Chemical Abstracts, vol. 66, No. 1, Jan. 2, 1967, p. 156, column 1.
Vojtíšek, V., et al., Preparation of L–Asparatic Acid by Means of Immobilized *Alcaligenes metalcaligenes* Cells, *Biotechnology and Bioengineering*, vol. XXVII, pp. 1072–1079, (1986).
Burdick, B., "Production of Specialty Chemicals Using Immobilized Whole Cells in Spiral–Wound Bioreactors", *Biotechnology and Bioengineering*, vol. 31, pp. 390–395, (1988).

* cited by examiner

*Primary Examiner*—Irene Marx
(74) *Attorney, Agent, or Firm*—Genencor International, Inc.

(57) ABSTRACT

The use of strains of the genus Microbacterium for the production of organic acids or amino acids by the enzymatic conversion of a fumaric acid to the organic acid or amino acid desired, as well as methods for such use and the conversion solution produced by such use and the methods of the present invention are disclosed. The uses and the methods of the present invention provide the L-isomer form of the desired organic acid or amino acid produced thereby in the absence of the D-isomer form of the desired organic acid or amino acid. Also disclosed are reactants solutions which include the strain of the genus Microbacterium and the L-isomer form of either the organic acid or the amino acid.

9 Claims, No Drawings

PRODUCTION OF ASPARTIC AND MALIC ACIDS WITH MICROBACTERIUM

This is a continuation of application Ser. No. 08/365,402 filed Dec. 28, 1994 now abandoned.

FIELD OF THE INVENTION

The present invention relates to the production of organic acids and amino acids, and in particular of L-malic acid and L-aspartic acid, with the use of microorganisms, and in particular with the use of species of microorganisms of the genus Microbacterium.

BACKGROUND OF THE INVENTION

Organic Acids and amino acids are used for a variety of purposes in the pharmaceutical, health and food industries. Especially preferred are the L-isomer forms of organic acids and amino acids.

L-malic acid is an organic acid that is used primarily in pharmaceutical applications as an antidote for hyper-ammoniemia and as a component of amino acid infusion. L-malic acid also presents interest as a food acidulant in competition with citric acid for, for example, confectionary products. Further uses include that of a flavoring agent in a wide range of foods such as nonalcoholic beverages, candy and canned fruits and vegetables.

L-aspartic acid is an amino acid widely utilized in the food industry as a flavoring agent.

Organic acids and amino acids have conventionally been produced by chemical synthesis. However, chemically synthesizing amino acids and organic acids (for example, the chemical synthesis of malic acid from maleic anhydride and water) generally produces the amino acid or the organic acid as an optically inactive mixture (DL-isomer). Such mixtures must then be subjected to a separation process to remove the natural L-isomer from the DL-mixture.

To overcome the problems associated with such DL-isomer mixtures, resort has been made to the use of various microorganisms to synthesize (produce) organic acids and amino acids. Such use of microorganisms provides a biospecificity and selectivity to the enzymatic reaction to permit conversion of a substrate to the natural L-form of the organic acid or amino acid which is generally unavailable in chemical synthesis. This biospecificity and selectivity offers advantages of total product yield, product quality and a significant reduction in waste disposal, production of the natural L-form of the organic acid and/or amino acid produced thereby.

The use of various microorganisms to enzymatically convert fumaric acid to the natural L-form of malic acid has been disclosed. Such strains include those of the species *Lactobacillus brevis, Lactobacillus delbrueckii* and *E. coli* (U.S. Pat. No. 2,972,566) and the genus *Paracolobacterium aerogenoides* (U.S. Pat. No. 3,980,520). Furthermore, the use of a variety of fumarase-producing microorganisms, such as *Brevibacterium ammoniagenes, Corynebacterium egui, Xanthobacter flavus, Proteus vulgaris* and *Pichia farinosa* (U.S. Pat. No. 3,922,195), have all been disclosed for the conversion of fumaric acid to malic acid.

The use of various microorganisms to convert fumaric acid (ammonium salt) to L-aspartic acid has also been reported. Strains of *E. coli, Brevibacterium metalcoligenes,* Serratia and *Pseudomonas putida* have all been disclosed for this purpose. Further, the use of *Brevibacterium ammoniagenes* to convert ammonium fumarate to L-aspartic acid has also been described in U.S. Pat. No. 4,138,292.

Unfortunately, while the biospecificity and selectivity of the enzymatic reaction using the disclosed microorganisms offers certain advantages relating to the production of the natural L-form of malic acid, aspartic acid and/or other organic acids and/or amino acids, there nonetheless remains a need to improve the efficacy of these processes and to identify and use previously unconsidered species of microorganisms therefor.

Microorganisms of the genus Microbacterium are well known and described [see Bergey's Manual of Systematic Bacteriology, Volume 2, Section 15 at Pages 1320–1322 (1986)]. Even though strains of Microbacterium are fumarase producers, we are not aware of the use of microorganisms of the genus Microbacterium for the production of L-malic and/or L-aspartic acid.

Accordingly, it can be seen that there remains a need to identify and utilize other microorganisms which are capable of efficiently and effectively producing organic acids and/or amino acids, such as L-Malic acid and/or L-Aspartic acid, on an industrial scale.

SUMMARY OF THE INVENTION

It is a primary object of the present invention to identify and provide microorganisms which are capable of efficiently and effectively converting fumaric acid or a salt thereof for the production of organic acids and/or amino acids and, in particular of L-malic acid and/or L-aspartic acid.

It is a further primary object of the present invention to provide a method for efficiently and effectively producing organic acids and/or amino acids and, in particular, of L-malic acid and/or L-aspartic acid.

It is a still yet further primary object of the present invention to provide organic acids and amino acids, and in particular, L-malic acid and L-aspartic acid, which have been enzymatically synthesized (produced) by the use of microorganisms.

In accordance with the teachings of the present invention, identified and utilized as disclosed herein are microorganism strains of the genus Microbacterium which are useful for the production of organic acids and/or amino acids by the enzymatic conversion of fumaric acid or a salt thereof.

In further accordance with the teachings of the present invention, disclosed herein is a method for the production of organic acids and/or amino acids. This method is comprised of culturing a strain of the genus Microbacterium, whereby fumarase is produced (intracellularly) thereby. If desired, the cultivated strain may then be recovered from the cultivation media. Cultivation is followed by reacting a fumaric acid or a salt thereof with the cultivated strain of the genus Microbacterium, whereby the fumaric acid or salt thereof is enzymatically converted to either the L-organic acid or the L-amino acid. This method further comprises recovering the said L-organic acid or L-amino acid so produced.

Preferably, the method of the present invention further includes immobilizing the microorganism before the placement thereof in the conversion solution in the presence of a fumaric acid or a salt thereof. However, it is noted that the method of the present invention may also be performed with the microorganism in a "free" form within the conversion solution.

It is further preferred that the immobilized microorganisms be pretreated before the use thereof for enzymatically converting the fumaric acid or salt thereof. In this regard, the method of the present invention further comprises incubating the immobilized microorganism in a pretreatment solution that includes the L-organic acid or L-amino acid to be produced therewith and a buffer. It is further preferred that such pretreatment incubation be conducted with gentle agitation. Preferably, the method of the present invention comprises culturing one of the following strains of the genus Microbacterium: *Microbacterium imperiale, Micobacterium lacticum, Microbacterium ammoniaphilum, Micobacterium arborescens* and *Microbacterium laevaniformans.*

Most preferably, the method of the present invention comprises culturing one of the following strains: *Microbacterium imperiale* ATCC 8365, *Microbacterium lacticum* ATCC 8180, *Microbacterium ammoniaphilum* ATCC 15354, *Micobacterium arborescens* ATCC 4358 and *Micobacterium laevaniformans* ATCC 15953.

It is further preferred that the fumaric acid to be used (enzymatically converted) in the method of the present invention is in a salt (fumarate) form thereof. Preferred is the use of either sodium fumarate or ammonium fumarate. In this regard, it is contemplated herein that the method of the present invention will comprise the enzymatic conversion of sodium fumarate by strains of the genus Microbacterium for the production of L-malic acid and the enzymatic conversion of ammonium fumarate by strains of the genus Microbacterium for the production of L-aspartic acid.

The organic acids and amino acids produced by the method of the present invention are in the natural L-isomer forms thereof. Most preferred is the use of the method of the present invention to produce L-malic acid and L-asparatic acid.

In another related aspect of the present invention, disclosed herein is a method for the production of L-organic acids and L-amino acids comprised of reacting the fumarase naturally produced by a strain of the genus Microbacterium with a fumaric acid or a salt thereof, whereby the fumaric acid or salt thereof is enzymatically converted to either the L-organic acid or the L-amino acid. This method includes the steps of culturing a strain of the genus Microbacterium, whereby fumarase is produced and recovering the fumarase. If desired, the fumarase may be recovered in a purified or concentrated form and with or without the presence of other constituents of the culture media, including cells of the producing organism (such as a Microbacterium or a genetically engineered host) or portions thereof. The recovered fumarase is then reacted with a fumaric acid or a salt thereof, whereby the fumaric acid or salt thereof is enzymatically converted to either the L-organic acid or the L-amino acid. This method further comprises recovering the said L-organic acid or L-amino acid so produced.

In yet further accordance with the teachings of the present invention, disclosed herein is a reactants solution which is comprised of a highly purified L-organic acid or an L-amino acid and cells of a strain of the genus Microbacterium which were employed in the conversion of fumaric acid or a salt thereof to the desired L-organic acid or L-amino acid and wherein no other form (i.e., DL-form) of the organic acid and/or amino acid is present.

The strains of Microbacterium in the reactants solution of the present invention are, preferably, *Microbacterium imperiale, Microbacterium lacticum, Microbacterium ammoniaphilum, Microbacterium arborescens* and *Microbacterium laevaniformans.*

It is most preferred for the reactants solution of the present invention to include the strains *Microbacterium imperiale* ATCC 8365, *Microbacterium lacticum* ATCC 8180, *Microbacterium ammoniaphilum* ATCC 15354, *Microbacterium arborescens* ATCC 4358 and *Microbacterium laevaniformans* ATCC 15953.

Preferably, the L-organic acids and the L-amino acids of the reactants solution of the present invention are L-malic acid and L-aspartic acid.

These and further objects and advantages of the present invention will become readily apparent upon a reading of the following description in conjunction with the Examples thereof.

DESCRIPTION OF PREFERRED EMBODIMENTS

The present invention involves the identification and the use of microorganisms, which offer a biospecificity and selectivity of the enzymatic reaction, for the production of L-organic acids and L-amino acids by the enzymatic conversion of a fumaric acid or a salt thereof.

The microorganisms which are identified and used for the production of the organic acids and/or amino acids by the conversion of a fumaric acid or a salt thereof according to the teachings of the present invention are those belonging to the genus Microbacterium. In particular, microrganisms of the species *Microbacterium imperiale, Microbacterium lacticum, Microbacterium ammoniaphilum, Microbacterium arborescens* and *Microbacterium laevaniformans* have all been identified and utilized herein as efficient and effective for this task. Most particularly, strains *M. imperiale* ATCC 8365, *M. lacticum* ATCC 8180, *M. ammoniaphilum* ATCC 15354, *M. arborescens* ATCC 4358 and *M. laevaniformans* ATCC 15953 are disclosed herein.

The method of the present invention involves the enzymatic conversion of fumaric acid or a salt thereof for the production of organic acids and/or amino acids and, in particular, the L-isomers thereof. A major advantage of the methods (and the conversion solution) of the present invention is that the organic acids and/or amino acids produced thereby are in the L-isomer form and not in the D-isomer form. In this regard, we note that the uses and methods of the present invention produce (a solution which has) the L-isomer form of the desired organic acid and/or amino acid in the absence of the D-isomer form, so that a substantially isometrically pure L-organic acid and/or L-amino acid is produced thereby and not a DL-isomer mixture.

The method of the present invention is comprised of selecting a suitable strain of the genus Microbacterium which strain is desired to be used for the enzymatic conversion desired to be carried out. This strain is then cultured in a culture broth (during which culturing the microorganism produces a fumarase). After culturing is completed, this strain is removed from the culture broth.

The cultured strain then placed (incubated) in a conversion solution which includes (in the presence of) a fumaric acid or a salt (fumarate form) thereof suitable for being enzymatically converted to the desired organic acid or amino acid. In the conversion solution, the fumarase produced by the strain of Microbacterium reacts with the fumaric acid or salt thereof, whereby the fumaric acid or salt thereof is enzymatically converted into the (L-isomer form of the) organic acid and/or amino acid whose production is desired and the reactants solution is formed. The organic acid and/or amino acid which is produced in this manner is then recovered (by separation) from the reactants solution for subsequent use as desired and/or needed.

The method of the present invention utilizes strains of the species *Microbacterium imperiale, Microbacterium lacticum, Microbacterium ammoniaphilum, Microbacterium arborescens* and *Microbacterium laevaniformans.* Most particularly, strains *M. imperiale* ATCC 8365, *M. lacticum*

ATCC 8180, *M. ammoniaphilum* ATCC 15354, *M. arborescens* ATCC 4358 and *M. laevaniformans* ATCC 15953 have been utilized in the method of the present invention.

The microorganisms can be cultured in any manner which permits the growth thereof (with the concurrent production of fumarase), as will be readily understood by one skilled in the art. In this regard, it is contemplated herein that such cultivation will be done under aerobic conditions in culture media which also contains sources of carbon (such as glucose, starch, glycerol and molasses), nitrogen (such as peptone, hydrolyzed derivatives of casein or soja, ammonium or sodium nitrates, ammonium sulphate or phosphate, corn steep liquor, malt extract, etc.) and, if desired, mineral salts. The temperature of such cultivation can be carried out at a temperature range of from about 20° C. to about 40° C. and, preferably, from about 30° C. to about 32° C. for a period of from about 18 to about 48 hours, depending upon the particular strain being cultivated. Preferred is to perform such cultivation for either 23 hours (in the case of where the strain is *M. imperiale*), 47 hours (in the case of where the strain is *M. laevansiformans* or 36 hours (for the remaining strains of Microbacterium which were used herein). The pH of the culture media may be from about pH 5.5 to about pH 8 with a pH of about 6–7 being preferable.

The cells may then be recovered at the end of fermentation (cultivation). Such recovery may be carried out by any suitable means therefor which are well known to those skilled in the art. As disclosed herein, such recovery is achieved by centrifugation of the culture broth so as to form a pellet containing the cells, followed by decanting of the supernatant or otherwise recovering the cells.

If desired, the recovered cells may be used as such (in a free form of bacterial cell) in the subsequent conversion (reaction). In such an event, it is contemplated herein that the cells would be broken according to one of the known methods and the raw extract or a partially purified extract thereof used in the conversion reaction.

Although the microorganism may be used in a free form of bacterial cell, it is advantageous to immobilize the bacterial cell (or the fumarase which the bacterial cell contains). In such an event, the bacterial cells may be immobilized while in (before the removal thereof from) the whole fermentation broth (and before the placement thereof in the conversion solution in the presence of a fumaric acid or a salt thereof). After such immobilization, the fermentation broth may be easily removed therefrom by any method well known to those skilled in the art, such as by simple decanting.

Immobilization of the bacterial cells may be done by any conventional method well-known to those skilled in the art, suitable to permit the use thereof in the enzymatic conversion of the fumaric acid (or a salt thereof) according to the method of the present invention. Such methods include being immobilized to a polyacrylamide or carrageenan gel or a high polymer film. Other methods of immobilization (and those which are preferably utilized herein) are those methods described in U.S. Pat. Patent No. 4,760,024.

The fumaric acid and the salts thereof to be used (enzymatically converted) in the method of the present invention may be any fumaric acid being in any form (such as a salt fumarate form) suitable for being enzymatically converted to the desired organic acid. In this regard, sodium, potassium, ammonium, calcium, magnesium and barium fumarates may all be employed as the salt form of the fumaric acid to be enzymatically converted. Preferred salts are sodium fumarate and ammonium fumarate. It is contemplated herein that sodium fumarate (and its enzymatic conversion by strains of the genus Microbacterium) will be utilized for the production of L-malic acid and that ammonium fumarate (and its enzymatic conversion by strains of the genus Microbacterium) will be utilized for the production of L-aspartic acid.

According to the method of the present invention, fumaric acid or a salt thereof is reacted with the fumarase produced by the cells in a solution (conversion solution). The fumaric acid or salt thereof has a pH of about 4 to about 10 with a pH of 7.5 being preferred in the event that L-malic acid is being produced by conversion of sodium fumarate and a pH of 8.8 being preferred in the event that L-aspartic acid is being produced by conversion of ammonium fumarate. The reaction may be carried out at a temperature of about 15° C. to about 60° C. (with a temperature of about 40° C. being preferred) for a period of about 0.5 to about 48 hours, with one hour being preferred.

The solution (the conversion solution) is comprised of the liquid form of the fumaric acid or the salt thereof which is desired to be converted. Preferably, this fumaric acid or salt thereof is present in a concentration of 1.0 M.

If desired, the (conversion) solution may also include water, an aqeuous solution of a solvent, such as phosphoric or trishydrochloric acid buffer solution. An alkali, such as sodium, potassium or ammonium hydroxide or an inorganic acid, such as hydrochloric or sulfuric acid may be added to the solution, so that it may have a pH of from about 4 to about 10 (and, preferably from about 7.5 to about 8.8).

Although there is no particular limitation as to the concentration of fumaric acid or salt thereof which is present in the (conversion) solution, so as to be subjected to the conversion reaction, it is usually appropriate to employ from between about 0.5% (w/v) to about 30% (w/v). 11.6% (w/v) is preferred.

Although there is no particular limitation as to the concentration of the cultured or treated product (such as the microorganism) to be included in the (conversion) solution, it is usually appropriate to employ about 0.5% (w/v) to about 10% (w/v) with concentrations of 4.0% (w/v) being preferred.

Any known method, such as adsorption and desorption using, for example, an ion exchange resin or active carbon can be employed for separating the L-organic acid or L-amino acid from the reaction product and refining it for subsequent use.

The conversion solution of the present invention includes a strain of a microorganism of the genus Microbacterium (which were particularized and discussed at length above) and either an L-organic acid or an L-amino acid in the absence of the D-isomer and/or the DL-isomer forms thereof. In this regard, the conversion solution is free of the presence of either the D-isomer and/or DL-isomer mixture forms of the organic acid or amino acid.

If desired, the principles of the present invention permit the production of L-organic acids and L-amino acids by reacting the fumarase which is naturally produced by a strain of the genus Microbacterium with a fumaric acid or a salt thereof, whereby the fumaric acid or salt thereof is enzymatically converted to either the L-organic acid or the L-amino acid.

By use of the term "naturally produced by" when referring to the fumarase what is meant is not only the fumarase when it is produced by the naturally producing microorganisms thereof (which have been identified herein) but also that same fumarase which has been produced by another microorganism by transformation thereof (using the well-known principles and techniques of genetic engineering) with the gene coding for the fumarase gene in such a manner so as to permit the expression by the genetically engineered host of the fumarase coded for by said gene.

Having thus described the uses, the methods and the conversion media of the present invention, the following examples are now presented for the purposes of illustration only and are neither meant to be, nor should they be, read as being controlling.

EXAMPLE 1

A fermentation media of 2 grams hydrolyzed animal collagen, 3 grams lactose and 1.5 grams bacto yeast extract (DIFCO) per 100 ml of distilled water (pH 6.0) was prepared. The media was sterilized at 120° C. for 30 minutes (liquid cycle) under 15 PSI and cooled.

Respective samples of the sterile fermentation medium were then innoculated with active culture (3% v/v) the various strains of Microbacterium listed in Table 1, all of which had been deposited in the American Type Culture Collection (ATCC), 12301 Parklawn Drive, Rockville, Md. 20852, U.S.A., under the accession numbers listed below in Table 1:

TABLE 1

| Microorganism | ATCC Accession Number | Sample # |
|---|---|---|
| M. imperiale | 8365 | 1 & 2 |
| M. lacticum | 8180 | 3 & 4 |
| M. ammoniaphilum | 15354 | 5 & 6 |
| M. arborescens | 4358 | 7 & 8 |
| M. laevaniformans | 15953 | 9 & 10 |

After innoculation of the respective samples as outlined in Table 1, fermentation was performed at 30–32° C. for either 23 hours (in the case of samples 1 and 2 for *M. imperiale*), 47 hours (in the case of samples 9 and 10 for *M. laevansiformans*) or 36 hours (for samples 3–8) in a thermostated benchtop incubated gyratory shaker G24 [¾" (19 mm) diameter circular orbit, rotated horizontally] maintained at 350 RPM.

EXAMPLE 2

The production of L-aspartic acid was achieved as follows.

The bacterial cells in the whole fermentation culture broth of samples 1, 3, 5, 7 and 9 were immobilized as described in Example 20 (and Table 2) of U.S. Pat. No. 4,760,024, but wherein 6N NaOH was utilized for pH adjustment.

A pretreatment solution was prepared consisting of (per 100 ml of water) 10% (w/v) L-aspartic acid (SIGMA), 0.1% (w/v) calcium chloride dihydrate, 0.1% (w/v) TWEEN-80 (SIGMA) and ammonium hydroxide (56.6% (w/w) for pH adjustment to 7.5). 10% (w/v) of the immobilized cells was then added to the pretreatment solution. These samples were then incubated for 6 hours at 40° C. with gentle agitation.

The pretreatment solution was then removed by decantation from the immobilized cells and the immobilized cells were resuspended in 50 ml portions of 1.0 M ammonium fumarate at pH 8.8 (thereby forming the conversion solution) for one hour at 40° C.

After one hour, the cells were separated from the reaction products (and the conversion solution) by centrifugation at 15000 RPM (SS-34 Rotor) for 45 minutes and the reaction products were analyzed by High Pressure Liquid Chromotography (HPLC) using an HPX-87C column (BIO-RAD) having a column temperature of 80° C. and using 0.01 M calcium acetate (pH 5.5) as mobile phase. RI detection was utilized as well as a flow rate of 0.9 ml/min. L-Aspartic acid production and concentration was then determined by calculating by comparison with standards obtained from a standard curve determined from the HPLC analysis.

The results of this method and use of the various strains of the genus Microbacterium are summarized below in Table 2.

TABLE 2

| Sample | Microorganism | L-Aspartic Acid Concentration (mg acid/hour/ml of broth) |
|---|---|---|
| 1 | M. imperiale ATCC 8365 | 258 |
| 3 | M. lacticum ATCC 8180 | 396 |
| 5 | M. ammoniaphilum ATCC 15354 | 438 |
| 7 | M. arborescens ATCC 4358 | 324 |
| 9 | M. laevaniformans ATCC 15953 | 390 |

The above HPLC analysis of the reaction products showed that the incubation of pretreated immobilized cells with ammonium fumarate at pH 8.8 produced L-aspartic acid.

EXAMPLE 3

The production of L-malic acid was achieved as follows.

The bacterial cells produced by the culturing of samples 2, 4, 6, 8 and 10 of Example 1 were collected from the culture broth by centrifugation of the samples at 15000 RPM (SS-34 Rotor) for 45 minutes. 2 grams of the wet bacterial cells of each of the samples which were so collected were then resuspended in respective 50 ml portions of 1.0 M sodium fumarate at pH 7.5 (thereby forming the conversion solution) for 1 hour at 40° C.

After one hour, the cells were separated from the reaction products (and the conversion solution) by centrifugation at 15000 RPM (SS-34 Rotor) for 45 minutes and the reaction products were analyzed by High Pressure Liquid Chromotography (HPLC) using an HPX-87H column (BIO-RAD) having a column temperature of 60° C. and using 0.01N sulphuric acid as the mobile phase. The flow rate was 0.7 ml/min. RI detection was utilized.

Malic acid production and concentration was then determined by calculating by comparison with standards obtained from a standard curve determined from the HPLC analysis.

The results of this method and use of the various strains of the genus Microbacterium are summarized below in Table 3.

TABLE 3

| Sample | Microorganism | L-Malic Acid Concentration (mg acid/hour/ml of broth) |
|---|---|---|
| 2 | M. imperiale ATCC 8365 | 3.6 |
| 4 | M. lacticum ATCC 8180 | 0.2 |
| 6 | M. ammoniaphilum ATCC 15354 | 1.8 |
| 8 | M. arborescens ATCC 4358 | 25.3 |
| 10 | M. laevaniformans ATCC 15953 | 0.2 |

The above HPLC analysis of the reaction products showed that the incubation of cells with sodium fumarate at pH 7.5 produced L-malic acid.

EXAMPLE 4

Bacterial cells of *M. arborescens* ATCC 4358 were obtained and cultured in the manner described above in Example 1, except that the quantities of the components utilized were increased by a factor of 100, so as to produce ten liters of fermentation broth. These bacterial cells were them immobilized according to the procedure and parameters described in Example 2 above (see Example 20, and Table 2 of U.S. Pat. No. 4,760,024), adjusted as necessary to account for the increased quantities. The ten liters of fermentation broth was then diluted with deionized distilled water until the electrical conductivity thereof measured less than 6000 ohms. The diluted broth was then mixed with 100 grams of FW-2 (Eagle-Picher) and mixed until a homogeneous solution is obtained (about 15–30 minutes). 630 ml of 5% (w/v) aqueous solution of polyethylenimine was added and the mixture was stirred until a homogeneous mixture was obtained (about 15 minutes) at pH 8.0.

Next, 2700 ml of 5% (w/v) chitosan was added and stirred until a homogeneous mixture was obtained (about 15 minutes) at pH 8.0.

800 ml of 5% (w/v) glutaraldehyde was added and the pH was adjusted to 9.0 using 6N sodium hydroxide.

The mixture was then gently stirred for one hour before being filtered (C. GOODMAN Co. cloth filter, catalogue #7418-0 polypropylene felt, 18 ounce felt double-glazed), extruded (die size: 1 mm) and dried at 45° C. in a Glatt Dryer (GLATT AIR TECHNIQUES, Inc.).

The dry immobilized cell particles were used for converting fumaric acid or a salt thereof to L-malic acid as follows.

The dry immobilized cell particle preparation was then charged into a jacketed column (2.5 cm×50 cm). Sodium fumarate solution (the conversion solution) at pH 7.5 (1M) was then continuously passed through the column at 40° C. at a flow rate of one-half the bed volume of the column per hour.

The L-malic acid content in the effluent was then determined by HPLC. The conversion rate of fumaric acid to L-malic acid was over 80%.

EXAMPLE 5

Bacterial cells of *M. arborescens* ATCC 4358 were obtained and cultured in the manner described above in Example 1, except that the quantities of the components utilized were increased by a factor of 100, so as to produce ten liters of fermentation broth. These bacterial cells were them immobilized according to the procedure and parameters described in Example 2 above (see Example 20, and Table 2 of U.S. Pat. No. 4,760,024), adjusted as necessary to account for the increased quantities.

The ten liters of fermentation broth was then diluted with deionized distilled water until the electrical conductivity thereof measured less than 6000 ohms. The diluted broth was then mixed with 100 grams of FW-2 (Eagle-Picher) and mixed until a homogeneous solution is obtained (about 15–30 minutes). 630 ml of 5% (w/v) aqueous solution of polyethylenimine was added and the mixture was stirred until a homogeneous mixture was obtained (about 15 minutes) at pH 8.0.

Next, 2700 ml of 5% (w/v) chitosan was added and stirred until a homogeneous mixture was obtained (about 15 minutes) at pH 8.0.

800 ml of 5% (w/v) glutaraldehyde was added and the pH was adjusted to 9.0 using 6N sodium hydroxide.

The mixture was then gently stirred for one hour before being filtered (C. GOODMAN Co. cloth filter, catalogue #7418-0 polypropylene felt, 18 ounce felt double-glazed), extruded (die size: 1 mm) and dried at 45° C. in a Glatt Dryer (GLATT AIR TECHNIQUES, Inc.).

The dry immobilized cell particles were used for converting fumaric acid or a salt thereof to L-aspartic acid as follows.

The dry immobilized cell particle preparation was then pre-incubated with a mixture of 10% (w/v) L-aspartic acid, 0.1% (w/v) calcium chloride dihydrate, 0.1% (w/v) TWEEN 80 (SIGMA) and concentrated (56.6 w/w) ammonium hydroxide (for pH adjustment) to pH 8.8. at 45° C. for five to eight hours with gentle stirring. The liquid was then decanted and the pretreated immobilized preparation were then packed in the column.

An aqueous solution (conversion solution) of ammonium fumarate (1M) at pH 8.8 was then passed through the column at 37° C. at a flow rate equal to ⅓ of the bed volume per hour. The L-aspartic acid was then precipitated by adjusting the pH of the effluent to pH 2.0–3.0 with concentrated sulphuric acid.

The L-aspartic acid content in the effluent was then determined by HPLC. The results of the above-described conversion is set forth in Table 4.

TABLE 4

| Flow rate (bed volume/hr) | L-Aspartic Acid Yield (% conversion of fumaric acid to L-aspartic acid) |
| --- | --- |
| 1.0 | 91.0 |
| 2.5 | 86.0 |
| 5.0 | 77.0 |
| 7.5 | 72.5 |
| 10.0 | 63.0 |

Accordingly it can be seen that the use of the method of the present invention resulted in efficient and effective enzymatic conversion of fumaric acid to L-aspartic acid.

Many modifications may be made without departing from the basic spirit of the present invention. Accordingly, it will be appreciated by those skilled in the art that within the scope of the appended claims, the invention may be practiced other than has been specifically described herein.

What is claimed is:

1. A method for producing L-aspartic acid or L-malic acid comprising, reacting fumaric acid or a salt thereof with a microorganism selected from the group consisting of *Microbacterium imperiale, Microbacterium lacticum, Microbacterium arborescens* and *Microbacterium laevaniformans,* whereby the fumaric acid or salt thereof is enzymatically converted to either the L-aspartic acid or L-malic acid.

2. The method of claim 1 wherein the microorganism is *Microbacterium imperiale* having ATCC accession number 8365.

3. The method of claim 1 wherein the microorganism is *Microbacterium lacticum* having ATCC accession number 8180.

4. The method of claim 1 wherein the microorganism is *Microbacterium arborescens* having ATCC accession number 4358.

5. The method of claim 1 wherein the microorganism is *Microbacterium laevaniformans* having ATCC accession number 15953.

6. The method of claim 1 wherein the fumaric acid or salt thereof is ammonium fumarate and wherein the ammonium fumarate is converted to L-aspartic acid.

7. The method of claim 1 wherein the fumaric acid or salt thereof is sodium fumarate and wherein the sodium fumarate is converted to L-malic acid.

8. The method of claim 1 further comprising recovering the L-aspartic acid or L-malic acid.

9. A method for producing L-aspartic acid or L-malic acid comprising:

reacting fumaric acid or a salt thereof with a *Microbacterium ammoniaphilum* having ATCC accession number 15354, whereby the fumaric acid or salt thereof is enzymatically converted to either the L-aspartic acid or L-malic acid.

* * * * *